(12) United States Patent
Bienvenu et al.

(10) Patent No.: US 6,412,481 B1
(45) Date of Patent: Jul. 2, 2002

(54) SEALED BACKPRESSURE ATTACHMENT DEVICE FOR NEBULIZER

(76) Inventors: Robert Bienvenu, 300 Aurora Dr., New Orleans, LA (US) 70131; Sam O'Rourke, 325 Brookmede, Gretna, LA (US) 70056

( * ) Notice: Subject to any disclaimer, the term of this patent is extended or adjusted under 35 U.S.C. 154(b) by 0 days.

(21) Appl. No.: 09/471,553

(22) Filed: Dec. 23, 1999

(51) Int. Cl.[7] .............................................. A61M 11/00
(52) U.S. Cl. ............................ 128/200.21; 128/203.16
(58) Field of Search ...................... 128/200.14, 200.16, 128/200.18, 200.21, 203.12, 203.16, 205.24, 912

(56) References Cited

U.S. PATENT DOCUMENTS

| | | | | |
|---|---|---|---|---|
| 3,903,884 A | * | 9/1975 | Huston et al. ............... | 128/194 |
| 4,231,973 A | * | 11/1980 | Young et al. ................. | 261/78 |
| 4,253,468 A | | 3/1981 | Lehmbeck | |
| 4,263,907 A | | 4/1981 | Lindsev | |
| 4,354,520 A | * | 10/1982 | Easley, Jr. ............. | 137/543.23 |
| 4,620,670 A | | 11/1986 | Hughes | |
| 4,787,655 A | * | 11/1988 | Gross et al. ................ | 285/151 |
| 4,823,784 A | * | 4/1989 | Bordoni et al. ........ | 128/200.14 |
| 5,020,530 A | | 6/1991 | Miller | |
| 5,062,419 A | * | 11/1991 | Rider .................... | 128/200.21 |
| 5,086,765 A | | 2/1992 | Levine | |
| 5,099,833 A | * | 3/1992 | Michaels ............... | 128/200.14 |
| 5,241,954 A | | 9/1993 | Glenn | |
| 5,425,358 A | * | 6/1995 | McGrail et al. ........ | 128/205.24 |
| 5,479,920 A | * | 1/1996 | Piper et al. ............ | 128/204.23 |
| 5,570,682 A | * | 11/1996 | Johnson .................. | 128/200.14 |
| 5,584,285 A | | 12/1996 | Salter et al. | |
| 5,598,835 A | | 2/1997 | von Schrader | |
| 5,613,489 A | * | 3/1997 | Miller et al. ........... | 128/203.28 |
| 5,630,409 A | * | 5/1997 | Bono et al. ............ | 128/200.18 |
| 5,655,520 A | * | 8/1997 | Howe et al. ........... | 128/203.12 |
| 5,752,502 A | * | 5/1998 | King ..................... | 128/200.18 |

* cited by examiner

Primary Examiner—John G. Weiss
Assistant Examiner—Teena Mitchell
(74) Attorney, Agent, or Firm—Keaty Professional Law Corporation

(57) ABSTRACT

An attachment for use with a nebulizer for delivery of aerosol medication to respiratory airways of a user has an elongated conduit provided with a one-way valve for admitting ambient air on one of its ends and a mouthpiece—on its opposite end. A calibrated pressure exhalation valve allows escape of exhaled gas once the pressure in the conduit exceeds a pre-determined setting of the valve. The outlet valve is spring-loaded and allows for various calibrations. The conduit is attachable to a nebulizer and facilitates build-up of positive pressure in the user's sealed airways to help maintain the airways distended for more effective delivery of the medication.

1 Claim, 5 Drawing Sheets

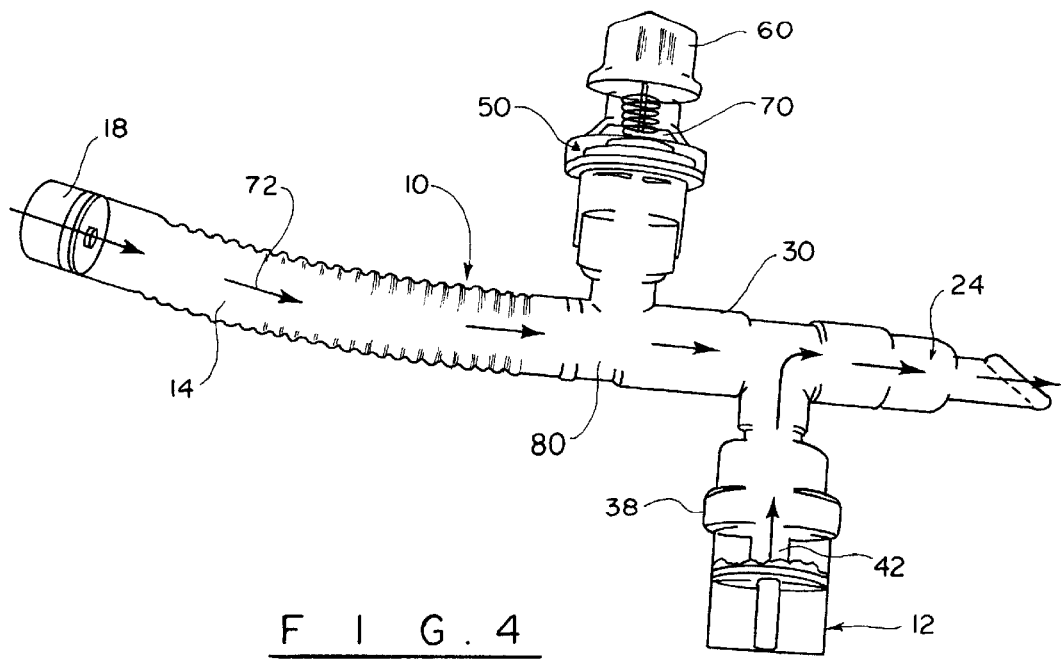
F I G. 4
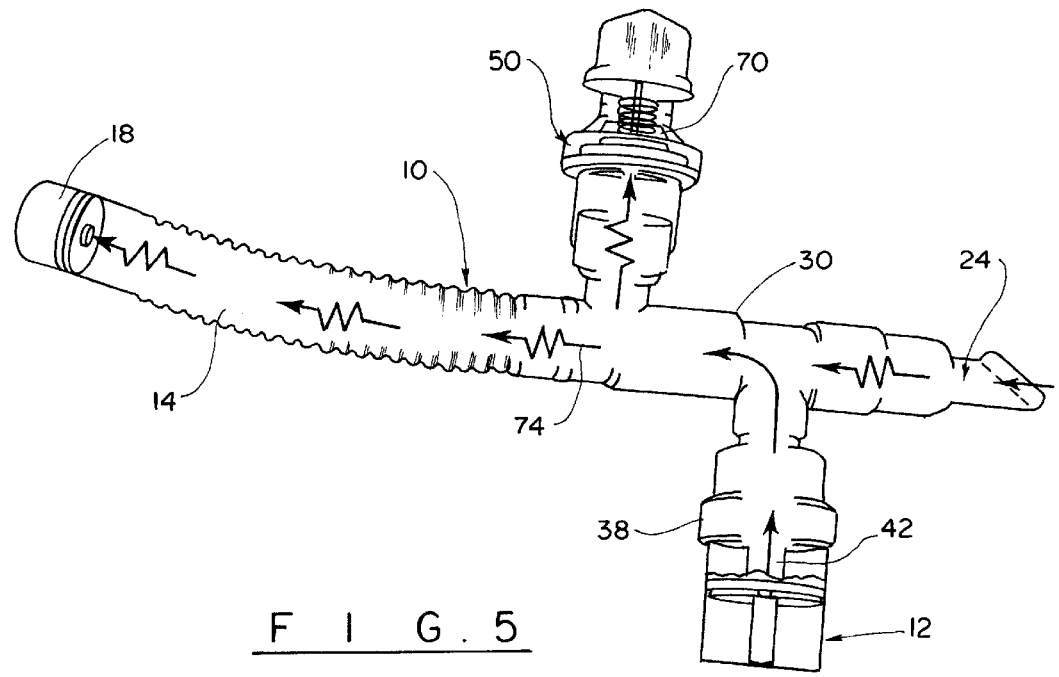
F I G. 5

SEALED BACKPRESSURE ATTACHMENT DEVICE FOR NEBULIZER

BACKGROUND OF THE INVENTION

The present invention relates to a breathing device adapted for use with a nebulizer for allowing a user to inhale medication particles generated by the nebulizer device through a sealed breathing attachment device. More particularly, the present invention relates to an attachment device for a nebulizer for generating positive backpressure in the airways of the user and to thereby keep the airways open for delivery of the medication to patient's lungs.

Nebulizers are widely used in the medical field for delivery of medicine to patient's lungs through inhalation. Nebulizers are conventionally used in an emergency, when conventional method dose inhalers (MDIs) fail to reverse a constriction in the airways. The nebulizer is designed to break down the liquid medication into small particles resembling mist. The patient, bringing the medication into the lungs and airways of the user, inhales this mist.

The medication that is aerosoled by a nebulizer usually contains a chemical that reacts with receptors in the bronchioles and causes the airways to dilate. The treatments with nebulizers can last up to several hours until the desired result is achieved. If the medication still doesn't reach the constricted areas in the lungs, stronger medications may be used. Depending upon the severity of the attack, the medications can include steroids, magnesium sulfate, and bronchodilaters.

Oftentimes, a patient delivered to an emergency room has a considerable concentration of carbon dioxide in the blood and the use of a nebulizer, which works relatively slow, may require up to eight hours of treatment, dictates that another type of an emergency device, an ambu bag with a mask, is used. The mask seals the area over the patient's mouth and nose allowing delivery of the aerosol medication. The mask forces the medication into the lungs by positive pressure generated by squeezing the ambu bag.

The positive pressure delivers air into the stomach of the patient, as well as into the lungs. When the air is diverted into the stomach it causes gastric distension and vomiting, which in turn, increases the risk of aspiration when the vomited medium is inhaled or forced into the lungs.

The most critically ill patients who do not respond to the treatment with conventional nebulizers or ambu bags are put on a ventilator, an artificial breathing machine that includes placing an endotrachial tube into the trachea of the patient. The tube has an inflated cuff for sealing the inhaling airway. Then the patient can be ventilated by positive pressure. Since the patient is sedated when he is on the breathing machine, the medication produced by the nebulizer can be more effectively delivered to the patient's lungs.

However, this drastic method suffers from serious disadvantages. The strong positive pressure drives the air into the lungs, sometimes causing damage by excessive pressure, or by excessive volume of air forced into the lungs. In some instances, the patient's inspiratory muscles atrophy, particularly in the case where the patient remains on the ventilator for a long period of time. The longer the patient stays on the ventilator, the more difficult it may be to "wean" the patient from the ventilator.

The present invention contemplates elimination of drawbacks associated with the prior art through the provision of a sealed back pressure attachment device for a nebulizer that creates positive pressure on the constricted airways and causes the airways to stay open for delivery of medication. With the use of the device according to the instant invention the patient's airways are incorporated into a closed circuit with the attachment device.

SUMMARY OF THE INVENTION

It is, therefore, an object of the present invention to provide a sealed back pressure attachment for a nebulizer device that would allow creation of positive end expiratory pressure on the constricted airways of a patient suffering from asthma, emphysema, or other respiratory illness.

It is another object of the present invention to provide a sealed backpressure slow breathing attachment device for a nebulizer that can be pre-set to create the desired amount of pressure within the device to help restore a person's breathing to their normal physiological state.

It is a further object of the present invention to provide an attachment device for a nebulizer that seals the backpressure and equalizes the pressure behind the terminal bronchial path.

It is still a further object of the present invention to provide a sealed backpressure attachment device for a nebulizer that can be calibrated for creating a predetermined amount of pressure in the airways of a patient.

It is still a further object of the present invention to provide a sealed backpressure attachment device for a nebulizer that is simple to use and inexpensive to manufacture.

These and other objects of the present invention are achieved through a provision of a sealed backpressure attachment device for a nebulizer that comprises a manifold and an elongated conduit/mixing reservoir made from a flexible resilient material. The conduit/reservoir has a one-way inlet valve for admitting ambient air into the conduit and a mouthpiece for engaging by a user's mouth. A spring-loaded calibrated adjustable pressure valve is mounted in fluid communication with the interior of the conduit to allow exhaled gases to be vented into the atmosphere.

A manifold is secured on the conduit between a mouthpiece and the calibrated pressure valve, the manifold having one portion that extends in a substantially co-axial relationship to the central axis of the conduit and a second portion that extends perpendicularly to the conduit central axis. The second portion of the manifold acts as a nebulizer connector in one embodiment and a nebulizer/pressure valve connector in the second embodiment. The manifold allows to detachably secure the sealed backpressure attachment device to a nebulizer. The manifold is mounted between the pressure valve and the mouthpiece.

When the user inhales, the ambient air is admitted into the conduit and draws aerosol medication from the nebulizer into the hollow conduit/mixing reservoir, delivering the medication into the mouthpiece and then into the user's respiratory system. When the user exhales, the one-way valve effectively prevents escape of exhaled gas through the first end of the conduit. Instead, the exhaled gas is diverted to the calibrated pressure exhalation valve, which is provided with an outlet port.

The gas pressure builds up until it is greater than the pre-set value of the valve. At that time, positive backpressure keeps exhaled gas in the user's sealed airways, which in turn causes collapsed or constricted air passages to stay open. Only after the pressure exceeds the pre-determined value the exhalation gas is allowed to escape into the atmosphere. Following this period, the medication particles are delivered into the lungs and airways of the patient, during inspiration.

The pressure exhalation valve may be preset in the range of between 5 cm of water to 10 cm of water although other pressure values may be used for the calibration of the valve, if desired. This application works because it is a sealed backpressure environment.

The present invention may be used as attachment for conventional nebulizers or, with certain modifications, with other respiratory emergency devices. The device of the present invention is believed to be particularly useful for asthma and emphysema sufferers, although other respiratory problems treatable with inhaled medications may benefit from the concept set forth in this application and the mechanical device disclosed herein.

BRIEF DESCRIPTION OF THE DRAWINGS

Reference will now be made to the drawings, wherein like parts are designated by like numerals, and wherein

FIG. 4 is a perspective view showing the airflow through the device of the present invention during inhalation.

FIG. 5 is a perspective view showing the airflow through the device of the present invention during expiration.

DETAILED DESCRIPTION OF THE PREFERRED EMBODIMENT

Figure 1:
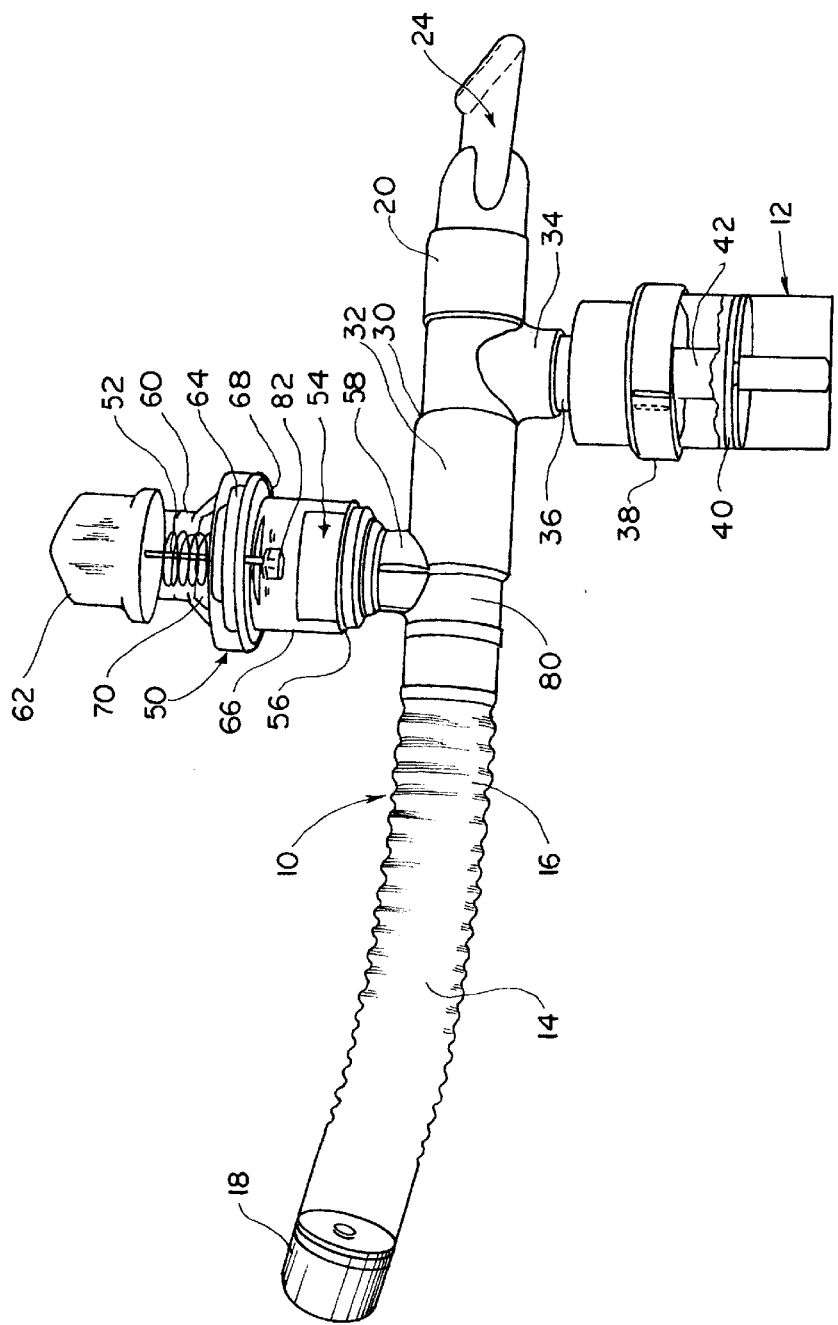
FIG. 1 is a perspective view of the attachment device according to the first embodiment of the present invention mounted on a standard nebulizer.

Turning now to the drawings in more detail, numeral 10 designates the attachment device in accordance with the first embodiment of the present invention. The device 10 is detachably secured to a conventional nebulizer 12 for operation. The device 10 comprises an elongated hollow conduit/mixing reservoir 14 made of a flexible, resilient material, such as for example, corrugated plastic tubing. The conduit 14 may be stretched through the expansion of corrugations 16 schematically shown in FIG. 1. The conduit 14 acts as a reservoir for collecting aerosolized medication. In this application, the words "conduit 14" and "reservoir 14" are used interchangeably.

A one-way valve 18 is mounted on one open end of the conduit 14 to allow intake of air from the exterior of the device 10. The one-way valve 18 prevents exhaled gases from escaping the conduit 14 during exhalation.

An opposite end 20 of the conduit 14 receives, in a frictional engagement, a mouthpiece 24. The mouthpiece 24 is detachably engaged, such as by threads (FIG. 3) to a manifold 30. The mouthpiece 24 is provided with an opening (not shown) permitting the user to inhale and exhale through the mouthpiece during operation of the device.

A three-way manifold 30 is mounted adjacent to the second end 20. The manifold 30 is provided with a first tubular member 32 that extends substantially coaxilly with a conduit 14 and a second, transverse member 34 that extends perpendicularly to the longitudinal axis of the conduit 14. The second portion 34 of the manifold 30 opens for direct communication with the interior of the conduit 14 for purposes, which will be explained in more detail hereinafter.

The second portion 34 of the manifold 30 is adapted for detachable engagement with an outlet cap 36 of the nebulizer 12. Since the nebulizer 12 can be any commercially available device, it is shown in a schematic view in FIGS. 1–6. Conventionally, the nebulizer 12 would have a hollow container 38 adapted for receiving liquid medication 40 inlet gas source therein. An aerosol-forming member 42 is positioned within the hollow housing 38 for drawing the medication from the housing 38 and forming droplets of liquid medication.

A fluid communication is established between the interior of the housing 38 and interior of the conduit 14 through the manifold 30 and the mouthpiece 24. Friction or any other similar means to the second portion 34 can attach the nebulizer device 12 when the device 10 is assembled with the nebulizer. It should be pointed out that the structure of the nebulizer 12 does not form a part of the present invention, and that attachment 10 may be used with other nebulizers available on the market.

A second three-way manifold 80 is mounted a distance from the first manifold 30. The second manifold secures a variable pressure valve 50, the interior of which is in fluid communication with the conduit 14 and the mouthpiece 24. The valve 50 is a one-way exhalation valve allowing exhaust gases to be vented to the atmosphere after exhalation by the user. The spring pressure valve 50 (PEEP valve) may be selected from a number of available valves made by different manufacturers.

The valve 50 has a spring 52 mounted therein to offer resistance to the opening of the valve during exhalation. The spring 52 is pre-set for controlling the amount of resistance offered to the gas flow and can be set to between 5 cm and 10 cm of water.

Of course, lower and higher values of the pressure may be set at the manufacturing facility, if desired, depending on the requirements of the medical practitioners. It is envisioned that the valves 50 may be color-coded, depending upon the calibration, with different colors corresponding to different values of pre-set pressure.

The valve 50 is mounted on the conduit 14 with the use of a perpendicular part 58 of the manifold 80. The member 58 frictionally seals the inlet 56 of the valve 50 and connects the valve 50 to the conduit 14. An exhaust opening 70 is formed in the valve 50 to allow exhaust gas to exit the attachment 10. An adjustable cap 62 of an upper housing 60 is threaded through a steel rod 82 against spring 52 engaged an enlarged diameter flange 64 to a lower portion 66 of the valve 50. The cap 62 is used to preset the tension on the spring 52 for controlling the pressure value in the conduit 14. The upper housing 60 may be frictionally fitted against an upwardly facing smaller diameter shoulder 68 formed on the body 66, as shown in FIGS. 1–6.

Figure 2:
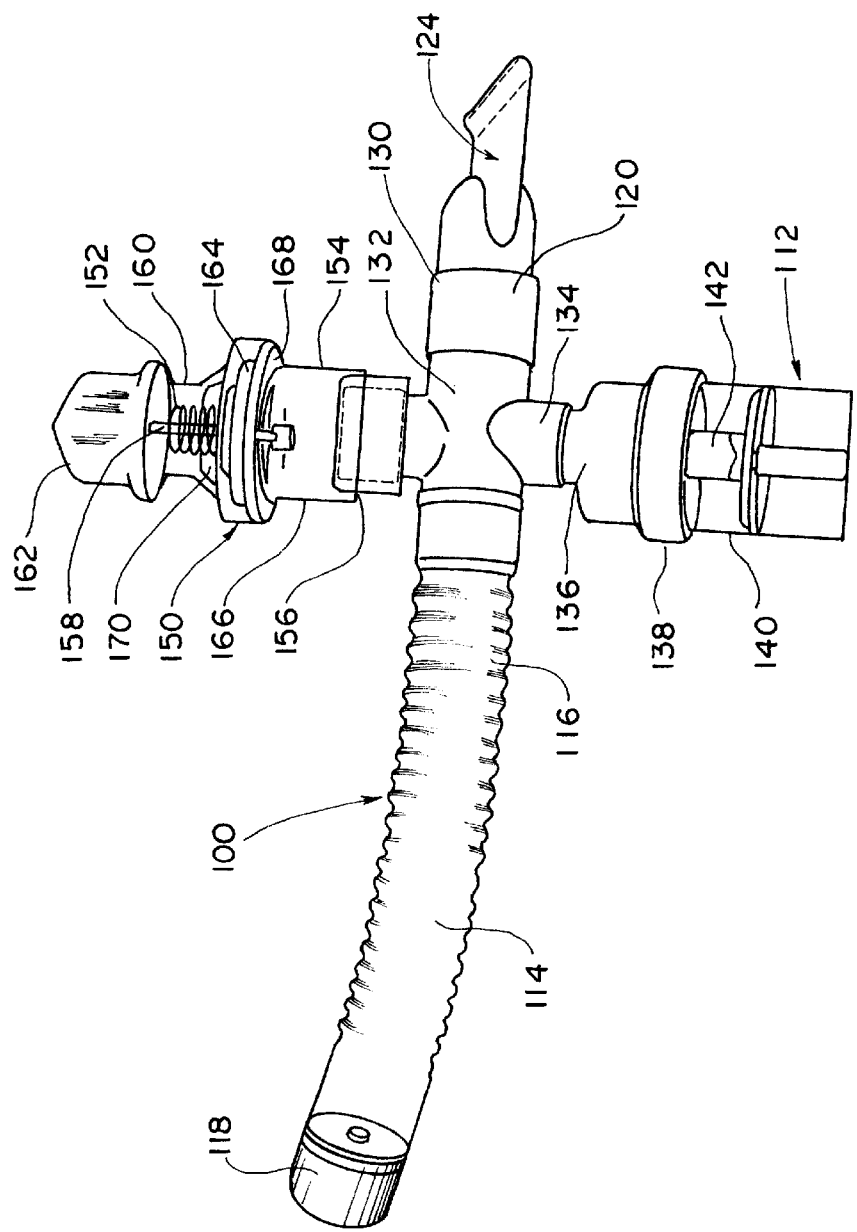
FIG. 2 is a perspective view of the second embodiment of the device in accordance with the present invention.
Figure 3:
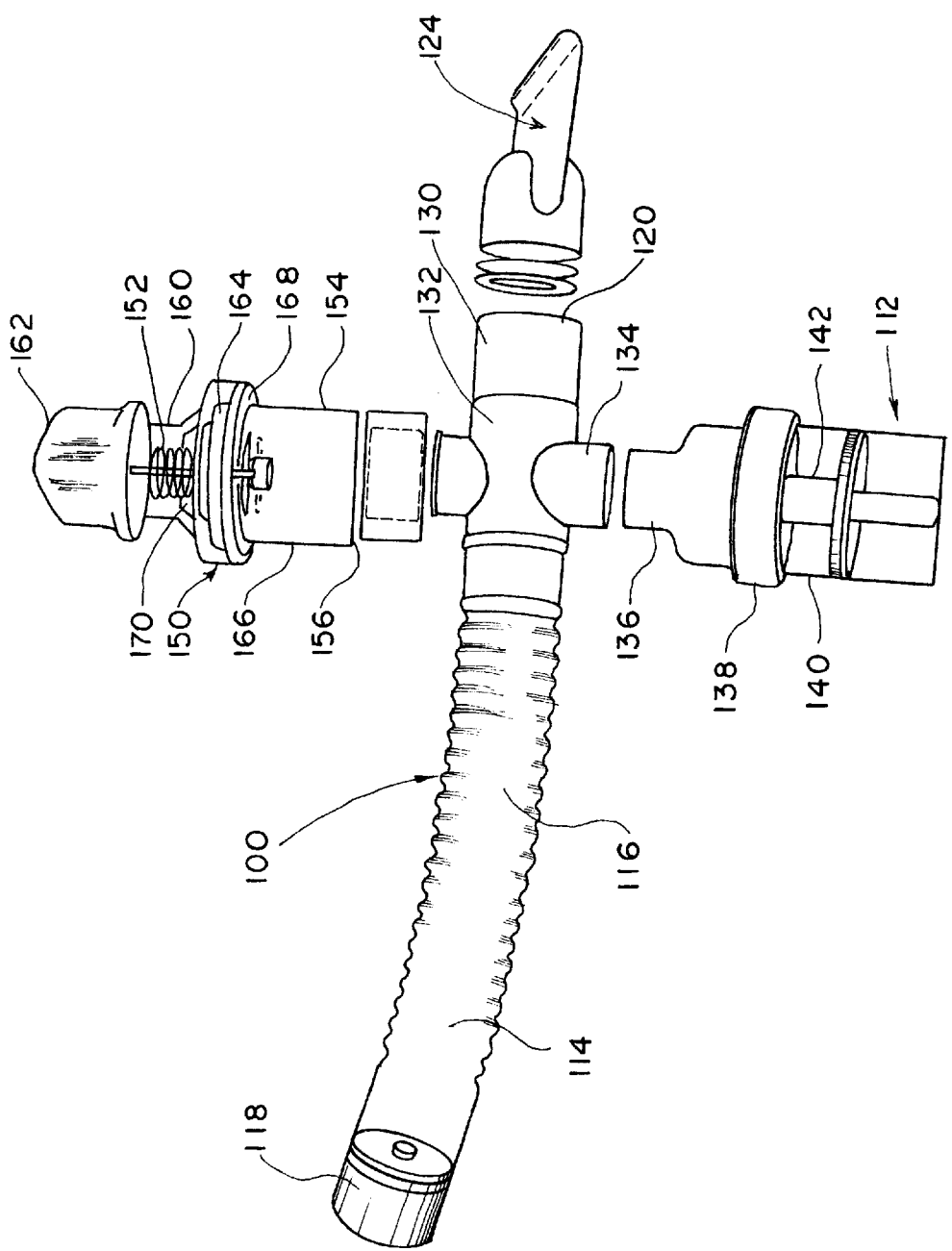
FIG. 3 is a partially exploded view of the second embodiment of the device of the present invention.

FIGS. 2 and 3 illustrate the second embodiment 100 of the device of the present invention. The device 100, similarly to the device 10, comprises an elongated conduit/mixing reservoir 114, a mouthpiece 124, an inlet one-way valve 118 and an exhalation one-way valve 150. In this embodiment, however, the manifold 130 is a four-way manifold that has a longitudinal portion 132 and a cross portion 134. In the second embodiment, the vertical axis of the exhaust valve 150 is oriented substantially co-axially with the center of the outlet cap 136 of the nebulizer housing 138.

Similarly to the device 10, the mouthpiece 124 is threadably engaged (see FIG. 2) with the manifold 130, and the portion 134 of the manifold 130 frictionally engages with the cap 136 of the nebulizer 112. The nebulizer 112 has medication source 140 and an aerosol forming member 142 mounted in the nebulizer housing 138.

The pressure exhalation valve 150 has a steel rod 158 carrying a spring 152 that is preset with the help of an adjustable cap 162. The second embodiment is more compact, with the conduit 114 being shorter than the conduit 14 since there is no length of tubing extending between the two manifolds, as in the first embodiment. Operation of both embodiments, however, is the same.

Turning now to FIGS. 4 and 5, the operation of the device 10 will be discussed in more detail. As can be seen in the drawings, when the user inhales, air is drawn from the atmosphere through the inlet valve 18 into the conduit 14. The airflow, schematically designated by arrows 72, travels directly through the reservoir 14, manifold 80, manifold 30 into the mouthpiece 24.

At the same time, the pressure created within the conduit 14 causes medication 40 to enter the aerosol-forming member 42 of the nebulizer 12 and move into the manifold 30, intercepting the airflow. The medication 40, having been mixed with air and broken into tiny droplets in the form of mist joins with the inlet airflow and is delivered into the airways of the user through the mouthpiece 24.

Figure 6:
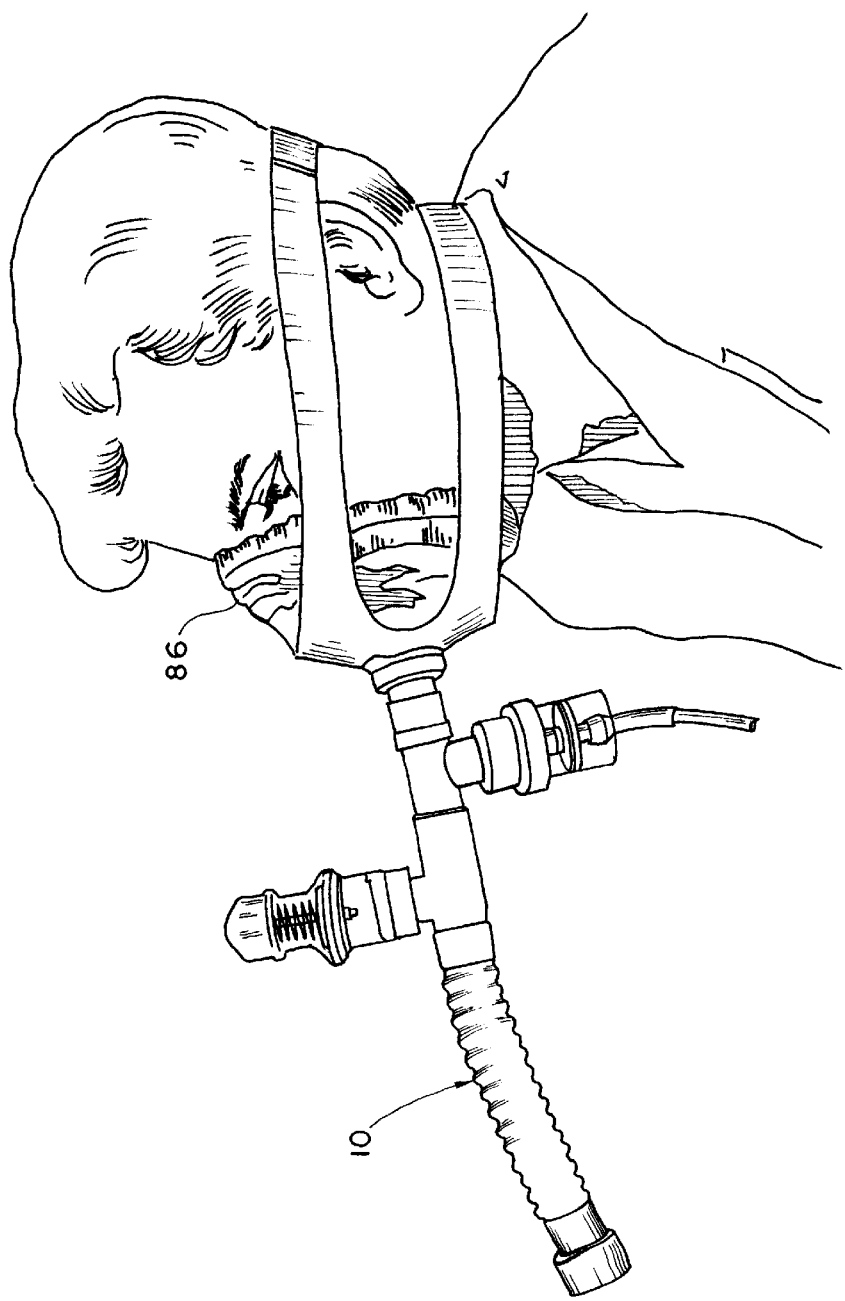
FIG. 6 is a perspective view of the device of the present invention as used with a face mask.

It is preferred, that during inhalation and exhalation, the patients have their lips closely sealed against the mouthpiece 24, so as to allow the device 10 to provide effective medication delivery and exhalation of gases. In the alternative, a facemask may be used, particularly with severely ill patients. This type of application is shown in FIG. 6.

During an asthma attack, medication often cannot reach the dilation receptors due to a massive bronchiole constriction and inflammation of the walls of the airways. If the medication cannot be directed to the affected area the constriction will continue to persist. With the attachment 10 of the present invention, when the patient exhales, the valve 50 that helps to distend airways and to prevent collapsing of the alveoli creates a positive backpressure.

When the positive back pressure is created in the conduit 14, the exhaled air is forced to exit only through the valve 50 that has been pre-set to offer resistance to the flow of gas being exhaled. The exhaust airflow, schematically illustrated by arrows 74 in FIG. 5, cannot exit through the valve 18 since it is a one-way valve. The spring loaded variable pressure exhalation valve 50 with its gas outlet port 70 becomes the only exit for the gas.

By keeping a sealed positive back pressure the airways are kept open. The device 10 allows trapped carbon dioxide to escape through the opening 70, thereby reducing hyper inflation and toxic levels of carbon dioxide in the bloodstream of the user. As the trapped gases are removed from the lungs, the lungs can generate a greater inspiratory pressure with less effort of the user.

Once the airways are. expanded, a pyramid effect begins to take place. A long expiratory phase is experienced allowing equalization of pressure and volume in all lung areas. Since the airway is stented it allows better air movement into the lungs and out of the lungs. The lungs are therefore not hyperinflated, allowing fresh air to enter the lungs. Consequently, the medicine 40 pulled in from the nebulizer 12 more effectively reaches the affected areas of the lungs, further dilating the airways.

The present invention can also be effectively used with patients suffering from emphysema. With such illness, the air spaces distal to the terminal bronchioles are weakened and are in a permanently enlarged condition. The alveolar walls are oftentimes damaged. The alveolar sac composed of tightly clustered alveoli disintegrates into larger air spaces. Because of the loss of alveoli, the amount of surface area for gas exchange is reduced and the elastic recoil of the lung tissue is compromised.

Emphysema patients have trouble exhaling because the alveoli no longer stretches and contracts with the same elasticity as in healthy lungs. Because of inadequate lung recoil, inspiratory muscles are fatigued. The lungs are unable to properly relax and return to their normal position. The inspiratory muscles remain somewhat contracted at the end of exhalation and, consequently, they are unable to fully contract with the next inspiration.

At the same time, if bronchial tubes are unable to support themselves against the pressure generated during the expiratory phase they tend to collapse. In cases like this, accessory muscle use with pursed lip breathing tends to create inconsistent back pressure, which may keep the bronchioles open. Using the attachment device 10 for the nebulizer 12, the patient can deliver the vital medication into the lungs and help dilate the airways.

The provision of the spring-loaded pressure exhalation valve 50 imitates "pursed lip breathing" when the patient exhales because backpressure is created by the valves 50 and 18. This backpressure prevents the bronchioles alveoli from collapsing. An open airway on exhalation allows for the escape of carbon dioxide reducing the level of that gas in the user's bloodstream.

When the exhaled gas escapes through the opening 70, the hyperinflation of the lungs is substantially reduced. The device 10 helps emphysema patients in a number of important ways. For example, the variable pressure valve 50 keeps the airways open, preventing the collapse of the alveoli and airways on expiration. As a result, the air is not trapped in the lungs and hyperinflation of airways is reduced.

The reduction in hyperinflation allows the user to inspire and exhale more fully, thereby delivering the medication 40 to a greater surface of the damaged tissue. Even further, by keeping the alveoli and airways open, the exhaled carbon dioxide moves more freely from the lungs into the atmosphere through the openings 70, 170 thereby reducing carbon dioxide levels in the user's bloodstream.

By creating positive backpressure within the conduit/reservoir 14 during exhalation, the air is not forced into the lungs and stomach of the user on inspiration. The backpressure, while not forcefully admitting air into the lungs and the stomach of the user, expands and keeps open the affected bronchial passages. This expansion allows for effective gas exchange as required for normal physiological function of the human body. The open air passages allow more medication and oxygen to be delivered into the lungs, substantially facilitating the treatment of obstructive pulmonary diseases.

It is believed that the present invention may assist other patients. with respiratory problems by creating a sealed positive backpressure and slowing the air movement that keeps the tubular airways dilated for delivery of the medication and exhaling of carbon dioxide. It is envisioned that the valves 50, 150 can be pre-set to greater values, particularly with patients having considerable problems with collapsed airways, although the preferred settings would range between 5 to 10 cm of water. By creating an artificial barrier to the exhalation of gas, the lateral wall pressure helps retain the walls in the distended condition, depending on the calibration set for the valves 50, 150.

It is within the scope of the present invention that the mouthpiece 24 can be replaced with a strapped facemask 86 on the end 20 of the conduit 14. The mask will be particularly useful in treating patients who are unable to assist medical personnel in controlling the seal around the mouthpiece. The mask covering mouth and nose of the patient may be available for use with patients that are unconscious or physically infirm to keep the lips tightly closed around the mouthpiece 24, to create a close circuit with the device.

It is further envisioned that the attachments 10, 100 of the present invention may be used for exercising the patients and restoring their ability to normally breathe. It is also envisioned that a nose clip and/or cushioned mouthpiece may be used in combination with the mouthpieces 24, 124 to better insure a sealed passageway between the conduits 14, 114 and the airways of the user.

By using a sealed backpressure environment, the sealed backpressure attachment devices 10, 100 of the present invention allows the patients to experience a long expiratory phase and keep the collapsed or obstructed airways open. This, in turn, allows delivering medication to the areas where the medication is needed most, to the sites affected by inflammation, constriction, and the like. Consequently, more precise medication delivery is achieved and the treatment is more effective with less medication.

Attachment devices 10, 100 of the present invention provides an effective alternative to the use of ambu bags where the air is artificially forced into the patient's body through the airways, reaching the lungs and stomach in a strong dynamic flow. The less traumatic creation of backpressure through the use of the present invention is therefore believed to be more beneficial for collapsed and obstructed airways of asthmatic and emphysema patients, as well as for persons suffering from other respiratory problems.

Many changes and modification may be made in the design of the present invention without departing from the spirit thereof. We, therefore, pray that our rights to the present invention be limited only by the scope of the appended claims.

We claim:

1. An attachment device for nebulizer designed to deliver aerosol medication for inhalation by a user, the attachment device comprising:

an elongated flexible resilient conduit having a first open end and a second open end;

a one-way valve mounted on the first open end of the conduit for admitting ambient air into the conduit while preventing escape of gas from the first open end of the conduit, said one-way valve being provided with an inlet opening oriented in a substantially co-axial relationship with a central longitudinal axis of said conduit;

a mouthpiece detachably secured on the second open end of the conduit for engaging by a mouth of the user during use of the device;

a calibrated outlet pressure valve mounted in fluid communication with an interior of said conduit, said valve allowing escape of a gas flow from said conduit during exhalation of the user after said gas flow pressure exceeds a predetermined value;

means for attaching the conduit to a nebulizer in fluid communication with said nebulizer; and a means for attaching said outlet pressure valve to said conduit said means comprising a four-way manifold positioned on said conduit and retaining said outlet pressure valve opposite said means for attaching the conduit to the nebulizer.

* * * * *